United States Patent [19]

Kitamura et al.

[11] Patent Number: 5,792,508
[45] Date of Patent: Aug. 11, 1998

[54] MATERIALS FOR TREATMENT OF PERIODONTAL DISEASE

[75] Inventors: Hiroyuki Kitamura, Moriguchi; Kazuaki Nishimura, Sakai; Mitsuru Nishigaki, Kyoto; Akira Yamaoka, Osaka; Etsuo Yoshikawa, Kitakatsuragi-gun, all of Japan

[73] Assignee: Kanebo Ltd., Tokyo, Japan

[21] Appl. No.: 615,233

[22] PCT Filed: Sep. 16, 1993

[86] PCT No.: PCT/JP93/01325

§ 371 Date: Mar. 15, 1996

§ 102(e) Date: Mar. 15, 1996

[51] Int. Cl.$^6$ ........................................ A61K 7/16
[52] U.S. Cl. .................. 424/49; 433/215; 433/217.1
[58] Field of Search ....................... 424/49–58; 433/215, 433/217.1

[56] References Cited

U.S. PATENT DOCUMENTS

| | | | |
|---|---|---|---|
| 4,524,824 | 6/1985 | Shimokobe et al. | 106/35 |
| 4,591,384 | 5/1986 | Akahane et al. | 106/35 |
| 4,961,707 | 10/1990 | Magnusson et al. | 433/215 |
| 5,032,445 | 7/1991 | Scantlebury et al. | 428/118 |
| 5,077,049 | 12/1991 | Dunn et al. | 424/426 |
| 5,093,179 | 3/1992 | Scantlebury et al. | 428/158 |
| 5,231,169 | 7/1993 | Constantz et al. | 530/356 |
| 5,238,491 | 8/1993 | Sugihara et al. | 106/35 |
| 5,324,519 | 6/1994 | Dunn et al. | 424/426 |
| 5,439,951 | 8/1995 | Glimcher et al. | 523/115 |
| 5,565,502 | 10/1996 | Glimcher et al. | 523/115 |

*Primary Examiner*—Shep K. Rose
*Attorney, Agent, or Firm*—Millen, White, Zelano, & Branigan, P.C.

[57] ABSTRACT

A material for treatment of periodontal disease which is comprised of cementum of a human or other animals combined with a bioabsorbable material.

16 Claims, No Drawings

MATERIALS FOR TREATMENT OF PERIODONTAL DISEASE

FIELD OF THE INVENTION

The present invention relates to materials for treatment of periodontal disease, and more specifically to materials for treatment of periodontal disease suitable for use for the treatment of severe periodontal disease which require periodontal surgery for regeneration of periodontal tissues and restoration of occlusive function.

PRIOR ART

Periodontal disease is an inflammatory disease in which dental supporting apparatus (gingiva, periodontal membrane, alveolar bone) is destroyed by dental plaque (a lump of bacteria), and it, along with dental caries, are said to constitute the two major diseases in the field of dentistry.

In this disease, the connecting tissue (periodontal fibers) between the tooth and gingiva is destroyed, resulting in pocket formation. As the disease progresses, this pocket becomes deeper and the alveolar bone is destroyed and absorbed. If this condition is left untreated, the tooth may in some cases fall out spontaneously.

With recent advancement in the treatment/prophylaxis of dental caries and progress toward the aging society, periodontal disease has attracted increasing attention and its treatment has become an important subject.

Severe periodontal disease requires reconstruction of the periodontal tissue by a surgical procedure. Its purposes are not only to remove the periodontal pocket but also to recover occlusive function through regeneration of the periodontal tissue destroyed by periodontal disease. A representative surgical technique currently performed is gingival flap operation. However, concerning the postoperative mode of healing, true attachment accompanied by neogenesis of the cementum (new attachment) is limited only to the apical region and ideal attachment is not achieved in other regions (epithelial attachment). Under these circumstances, various techniques have recently been attempted to positively achieve new attachment. They include, for example, root decalcification with citric acid and the like, root treatment using an extracellular matrix, guided tissue regeneration technique (GTR technique), and grafting of a tooth with attached cultured periodontal membrane cells to its root. However, none of these methods are satisfactory as remedies.

Among these techniques, the GTR technique is a method in which invasion of the epithelium and gingival connective tissue, which is considered to disturb postoperative new attachment, is physically eliminated and cells derived from the periodontal membrane, which is thought to be responsible for formation of the cementum, are selectively utilized. This technique has begun to be applied in general clinical practice in the U.S.A. and Sweden. This technique may be summarized as follows.

The pocket formed by periodontal disease is surgically excised, the gingival flap is separated and the contaminated cementum corresponding to the pocket is completely scaled off. Then, a membrane is inserted between the tooth and the gingiva, and the gingiva placed on the membrane is sutured.

This technique is based on the conception that the intervention of the membrane accelerates (upward) growth of periodontal cells remaining in the apical region toward the crown region, thereby facilitating new attachment.

Although data from animal experiments and clinical tests have been published indicating usefulness of this technique, clinicians do not put full reliance on it. The reasons are: that a question arises as to the conception which is the basis of this technique, that handling of the membrane and intraoperative management are difficult, and that data denying the usefulness of the membrane have been published (though an improvement has been made from the early unabsorbable membranes to absorbable ones).

DISCLOSURE OF THE INVENTION

The present invention has been made under these circumstances and its objective is to provide materials for treatment of periodontal disease, and in particular, to provide, on an industrial basis and at inexpensive prices, high-performance materials for treatment of periodontal disease, which are suitable for treatment of severe periodontal disease requiring periodontal surgery for regeneration of the periodontal tissue and recovery of occlusive function.

The above-mentioned objectives can be achieved by materials for treatment of periodontal disease which are comprised of tooth cementum from a human or other animals combined with a bioabsorbable material.

The present invention will be described in further detail below.

The cementum is a hard tissue resembling the bone, which covers the surface of the root of the tooth of animals higher than alligators. Recent studies have revealed that cementum has an ability of activating periodontal cells. Studies are being conducted for the exploration and utilization of its active components but have not led to a practical application thereof.

The present inventors have performed many studies on the utilization of the ability of cementum to activate periodontal cells and, as a result, found a technique comprised of combining it with a bioabsorbable material, thus achieving the present invention.

The cementum will be described in a little more detail. It is 50–240 µm thick. As to location, when viewed from the periodontal membrane side, the cementoblasts, the precementum and the cementum are located in order, and the dentine underlies the cementum. In this invention "cementum" means the precementum and the non-cellular cementum, and the non-cellular cementum may be used most preferably. While human cementum is most preferably used in this invention, bovine and porcine cementum is also preferable in view of easy availability which is a necessary requirement as a raw material.

The material for treatment of periodontal disease of the present invention is comprised of the above-mentioned cementum combined with a bioabsorbable material, wherein the "bioabsorbable material" in the present invention means a material that, when used as a material for treatment of periodontal disease in periodontal surgery, is decomposed and absorbed within a certain period of time through contact with the gingival tissue. As such materials, naturally occurring or synthesized materials may be used which are generally known as bioabsorbable polymers. The examples of such materials include gelatin, collagen, fibrin and the like as for naturally occurring materials, and polyglycolic acid, polylactic acid and their copolymers and the like as for synthesized materials.

The bioabsorbable material used in the present invention may be in a membranous or granular form, the former being more preferred considering its application onto the surface of the root. In the case of a membranous form, a porous membrane is more preferred than a simple plain membrane because of the greater amount of cementum retained in the former. Furthermore, in the case of porous membrane, it is preferable to have the pores communicated with each other in the direction of the thickness of the membrane, and, for adhesion to the surface of the root, it is preferred to include a thin membrane in one of its surfaces.

The reason for this is not only that such porous membrane has higher capacity and power for retention of cementum but that because of the communicated pores, when clinically applied, there may be less obstacles against migration of cells of the injured site toward the root side. Moreover, this is because the thin membrane in one of the surfaces gives stable adhesion to the surface of the root and thereby makes surgery easier, and because this thin membrane will be rapidly absorbed after the operation and thus allow cells to rapidly adhere to the surface of the root to establish adhesion of the gingival connective tissue. For such a porous membrane of bioabsorbable material, a double-layered bioabsorbable sheet made of a bioabsorbable material is suitable which is formed of a thin layer in one of its surface and formed of a wall having open pores in the other surface.

While such a double-layered bioabsorbable sheet may be produced from any of the above-mentioned bioabsorbable materials, gelatin and collagen are preferred because of their experience as biomaterials, and, in particular, the gelatin-based one is preferred, because it is readily available and inexpensive. An example of such sheet of gelatin is a double-layered gelatin sheet made of cross-linked gelatin which is formed of a dense thin layer on one of its surfaces and formed of a wall having open pores on the other surface (the double-layered gelatin sheet proposed in JP-A-4-135483).

The material for treatment of periodontal disease of the present invention is comprised of the above-mentioned cementum combined with a bioabsorbable material. For "combining" in the present invention, the cementum may be either included within the bioabsorbable material, e.g. a membrane made of the bioabsorbable material, or present on the surface of the membrane. In the former case it may be prepared by a method, for example, which comprises mixing a membrane raw material with the cementum and then forming the mixture into a membrane, and in the latter case it may be prepared by a method, for example, which comprises first forming a membrane, then pouring to spread the cementum, e.g. in suspension form, on it and then drying.

The material for treatment of periodontal disease of the present invention is advantageously used in periodontal surgery, in particular in gingival flap operation. That is, generally following flap formation and scaling, the material for treatment of periodontal disease of the present invention cut into an appropriate size is applied onto the surface of the root. As the material for treatment will readily adhere closely to the surface of the root, the operation will be completed simply by suturing the gingiva over the material. Because the material for treatment of periodontal disease of the present invention is comprised of the cementum combined with a bioabsorbable material, it may be left behind without the need of a further surgery to remove it, as is required in the case of an unabsorbable membranous material used in other cases.

In addition, while aesthetic demands are increasing among patients with periodontal disease in recent years, the material for treatment of periodontal disease of the present invention may be favorably used in muco-gingival surgery such as free gingiva grafting and pedicellate laterally repositioned flap operation, and thus enabling recovery of healthy gingiva onto the surface of the root exposed in the course of progression of periodontal disease.

As mentioned hereinbefore, the material for treatment of periodontal disease of the present invention has an ability of activating cells as it is comprised of the cementum combined with a bioabsorbable material. It makes it possible for periodontal tissue to regenerate, which has been impossible with other materials.

In addition, as it employs a bioabsorbable material and therefore spontaneously absorbed after surgery by simply leaving it behind, no further surgery is needed and thus the burden to the patient, both in pain and cost, may be lightened.

Moreover, it is very valuable for clinical use because it can be made stable and inexpensive by suitable selection of a bioabsorbable material.

Next, the present invention will be explained specifically with reference to an example.

EXAMPLE

Preparation of a Cementum-Combined Membrane

To a 5% aqueous solution of commercially available gelatin (viscosity 28 mp, jelly toughness 96 g (6.66%), Nippi Inc.) was added 3% by weight (relative to the gelatin) of glycerol polyglycidyl ether (Nagase Chemicals Ltd.) to dissolve. The mixture solution was poured to spread on a 2 mm-thick polymethylmethacrylate plate framed with an adhesive tape in an amount of 2 g/64 cm$^2$ and cooled to allow gelation for 20 minutes on a horizontal support kept at 5° to 10° C. Then, it was placed on a plate kept at −70° C. to allow freezing by cooling from its lower side, and then it was lyophilized at a temperature not higher than 25° C. After drying was completed, it was subjected to heat treatment at 110° C. for 2 hours. Then, this membrane was washed with distilled water at 50° C. and lyophilized again. The membrane thus formed was generally porous and double-layered and it included a thin membrane of about 1 μm on one of its surfaces and a large number of open pores in the other surface. The walls of the pores were oriented generally perpendicularly to the sheet plane. The mean thickness of the sheet was 180 μm.

Then, the membrane was placed on its thin layer side on a polymethylmethacrylate plate and a suspension of bovine tooth cementum was poured to spread on it in an amount of 0.24 mg/cm$^2$. After allowing to stand for 30 minutes to deposit the cementum, the membrane was subjected to lyophilization.

The bovine tooth cementum used in this experiment was prepared in the following manner.

The teeth were extracted with dental extracting forceps from the bovine jaw supplied from a slaughterhouse and stored frozen at −4° C. After thawing, attached soft tissue was immediately removed. At that time, to prevent the contamination with soft tissue in collecting cementum,a superficial layer of the cementum was also scraped off. After these procedures, curettage of the cementum was performed, 100–200 strokes per tooth, using a surgical scaler (the thickness of the bovine cementum is about 400–500 μm and the curettage amounting to even this number of strokes does not reach the dentine, the underlying layer). The cementum removed was collected in a 25-ml tube containing physiological saline. Then, after centrifugation, the supernatant physiological saline was discarded and the bottom abraded cementum pieces were dried spontaneously in a clean bench. Then, the dried cementum was placed in a mortar and pulverized with a pestle as far as possible to make cementum particles.

Periodontal Tissue Regeneration Experiment

After the buccal mucoperiosteal flap of each of the right and left maxillary lateral incisors and second premolars was separated from a Japanese monkey having completed permanent dentition, the alveolar bone in the buccal side was removed by 4 mm in the apical direction. At that time, in order to make the bone defect a form of dehiscence model, the interdental alveolar bone was completely removed. Then scaling and root planing were performed on the exposed root surface to eliminate the cementum. Subsequently, the Example cementum-combined gelatin membrane was applied to the left maxillary lateral incisor and second premolar, while the Control membrane which contained no cementum was applied to the right maxillary lateral incisor and second premolar, and the gingival flap was returned to the original position, followed by suture.

The Japanese monkey was sacrificed 3 weeks postoperatively and fixed by perfusion and tissue blocks were then isolated. According to the routine procedure, paraffin sections were prepared, H-E stained and examined histologically.

Gingival recession was scarcely observed regardless of the use of Example membrane or Control membrane. Also, downward proliferation of the epithelium toward the apical region was scarcely noted for either membrane.

The common mode of attachment following gingival flap operation is epithelial attachment by long junctional epithelium, but with Example membrane, new attachment accompanied by ideal regeneration of the cementum was achieved. In addition, bone regeneration toward the tooth crown, which was scarcely found with Control membrane, was remarkable, and periodontal fibers were seen passing horizontally between the corresponding root surfaces, indicating complete regeneration of the periodontal tissue.

On the other hand, the mode of attachment with Control membrane was due to gingival connective tissue and no regeneration of the cementum was found on the root.

We claim:

1. A material for treatment of periodontal disease which is comprised of cementum combined with a bioabsorbable material.

2. The material of claim 1, wherein said bioabsorbable material is gelatin, collagen, fibrin, polyglycolic acid, polylactic acid, or a glycolic acid/lactic acid copolymer.

3. The material of claim 1, wherein the cementum is human, bovine or porcine cementum.

4. The material of claim 2, wherein the bioabsorbable material is in the form of a porous membrane.

5. The material of claim 4, wherein the porous membrane of bioabsorbable material has a side with open pores at the surface and a more dense thin layer on the opposing side.

6. The material of claim 4, wherein the porous membrane of bioabsorbable material is a double-layered sheet of cross-linked gelatin having a dense thin layer on one surface and open pores on the opposing surface.

7. The material of claim 4, wherein said cementum is uniformly dispersed in said porous membrane.

8. The material of claim 4, wherein said cementum is deposited on the surface of said porous membrane.

9. A method of inducing regeneration of periodontal tissue wherein the material of claim 1 is used.

10. A method of inducing regeneration of periodontal tissue wherein the material of claim 2 is used.

11. A method of inducing regeneration of periodontal tissue wherein the material of claim 4 is used.

12. A method of inducing regeneration of periodontal tissue wherein the material of claim 5 is used.

13. A method of inducing regeneration of periodontal tissue wherein the material of claim 7 is used.

14. A method of inducing regeneration of periodontal tissue wherein the material of claim 8 is used.

15. The method of claim 9, wherein the material is placed on the surface of the root during a gingival flap operation.

16. The method of claim 12, wherein the dense thin layer of the material is placed an the surface of the root during a gingival flap operation.

* * * * *